United States Patent
Shen et al.

(10) Patent No.: US 9,188,579 B2
(45) Date of Patent: Nov. 17, 2015

(54) SNIFFING SMARTPHONE

(71) Applicant: QUALCOMM Incorporated, San Diego, CA (US)

(72) Inventors: Jian Shen, San Diego, CA (US); Tongzeng Yang, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 74 days.

(21) Appl. No.: 14/086,887

(22) Filed: Nov. 21, 2013

(65) Prior Publication Data

US 2015/0141073 A1    May 21, 2015

(51) Int. Cl.
*H04M 11/00* (2006.01)
*G01N 33/497* (2006.01)
*H04M 1/21* (2006.01)
*H04M 1/725* (2006.01)

(52) U.S. Cl.
CPC ............... *G01N 33/497* (2013.01); *H04M 1/21* (2013.01); *H04M 1/72569* (2013.01)

(58) Field of Classification Search
CPC .......................... H04M 11/002; H04M 1/0202
USPC ............ 455/556.1, 556.2, 557; 73/1.02, 23.3, 73/23.34, 23.36
See application file for complete search history.

(56) References Cited

U.S. PATENT DOCUMENTS

| | | | |
|---|---|---|---|
| 8,280,436 B2 | 10/2012 | Harris, Jr. | |
| 8,453,601 B2 | 6/2013 | Zimmerman | |
| 2004/0239510 A1 | 12/2004 | Karsten | |
| 2008/0314226 A1 | 12/2008 | Shibata | |
| 2010/0234064 A1 | 9/2010 | Harris, Jr. | |
| 2011/0181421 A1 | 7/2011 | Nabata et al. | |
| 2012/0278074 A1* | 11/2012 | Burke et al. | 704/235 |
| 2013/0125617 A1 | 5/2013 | Gouma et al. | |
| 2013/0192338 A1* | 8/2013 | Mayer et al. | 73/23.3 |
| 2013/0310110 A1* | 11/2013 | Forutanpour et al. | 455/556.1 |
| 2014/0118104 A1* | 5/2014 | Sicurello et al. | 340/3.1 |
| 2014/0139665 A1* | 5/2014 | Pinapala Venkata et al. | 348/143 |
| 2014/0349707 A1* | 11/2014 | Bang | 455/556.1 |

FOREIGN PATENT DOCUMENTS

| | | |
|---|---|---|
| GB | 2401752 A | 11/2004 |
| WO | WO-2012153124 A1 | 11/2012 |

OTHER PUBLICATIONS

International Search Report and Written Opinion—PCT/US2014/065311—ISA/EPO—Feb. 5, 2015.

* cited by examiner

*Primary Examiner* — Cong Tran

(74) *Attorney, Agent, or Firm* — Foley & Lardner LLP

(57) ABSTRACT

A wireless communication device having a breath sensor and a proximity sensor to measure the distance from a user to the device. The breath sensor is configured to measure or detect various components in the user's breath that may be indicative of a health issue. The sensitivity of the sensor may be adjusted based upon the proximity of the user. Sensor detections may be communicated in messages to a cloud server, where the cloud server may generate warnings if the messages indicate a health issue.

27 Claims, 3 Drawing Sheets

SNIFFING SMARTPHONE

FIELD OF DISCLOSURE

The invention relates to wireless communication devices, such as cellular phones, and more particularly to wireless communication devices with sensors to detect or measure the user's breath to monitor health.

BACKGROUND

Many health issues may be detected by analyzing a patient's breath. With advanced wireless communication devices such as smartphones almost ubiquitous in everyday life, it is of utility to provide such wireless communication devices with the capability to monitor the user's breath for health issues.

SUMMARY

Embodiments of the invention are directed to systems and methods for using a wireless communication device to measure or detect analytes that may indicate health issues associated with the user of the wireless communication device.

In an embodiment, a wireless communication device includes: a first sensor to detect an analyte associated with a user of the wireless communication device; a second sensor to measure a proximity of the wireless communication device to the user's mouth; and an application processor to set a detection threshold for the first sensor based upon the measured proximity.

In another embodiment, a system includes a server; and a wireless communication device. The wireless communication device includes: a first sensor to detect an analyte associated with a user of the wireless communication device; and an application processor programmed to send at least one message to the server, each message in the at least one message in response to the first sensor detecting an analyte in the breath of a user of the wireless communication device.

In another embodiment, a method includes: enabling a sensor to detect an analyte in the breath of a user of a wireless communication device, the first sensor embedded in the wireless communication device; sending by the wireless communication device at least one message to a cloud server, the at least one message indicating detections of the analyte by the first sensor; and generating by the server a warning message if the at least one message exceeds a threshold indicative of a health issue.

In another embodiment, a wireless communication device includes: a means for sensing breath, the means for sensing breath to detect an analyte associated with a user of the wireless communication device; a means for sensing proximity, the means for sensing proximity to measure a proximity of the wireless communication device to the user's mouth; and an application processor to set a detection threshold for the means for sensing breath based upon the measured proximity.

In another embodiment, a computer readable storage medium has stored instructions. The stored instructions, when executed by at least one processor, cause a system to perform a method comprising: enabling a sensor to detect an analyte in the breath of a user of a wireless communication device, the first sensor embedded in the wireless communication device; sending by the wireless communication device at least one message to a cloud server, the at least one message indicating detections of the analyte by the first sensor; and generating by the server a warning message if the at least one message exceeds a threshold indicative of a health issue.

BRIEF DESCRIPTION OF THE DRAWINGS

The accompanying drawings are presented to aid in the description of embodiments of the invention and are provided solely for illustration of the embodiments and not limitation thereof.

DETAILED DESCRIPTION

Aspects of the invention are disclosed in the following description and related drawings directed to specific embodiments of the invention. Alternate embodiments may be devised without departing from the scope of the invention. Additionally, well-known elements of the invention will not be described in detail or will be omitted so as not to obscure the relevant details of the invention.

The term "embodiments of the invention" does not require that all embodiments of the invention include the discussed feature, advantage or mode of operation.

The terminology used herein is for the purpose of describing particular embodiments only and is not intended to be limiting of embodiments of the invention. As used herein, the singular forms "a", "an" and "the" are intended to include the plural forms as well, unless the context clearly indicates otherwise. It will be further understood that the terms "comprises", "comprising", "includes" and/or "including", when used herein, specify the presence of stated features, integers, steps, operations, elements, and/or components, but do not preclude the presence or addition of one or more other features, integers, steps, operations, elements, components, and/or groups thereof.

Further, many embodiments are described in terms of sequences of actions to be performed by, for example, elements of a computing device. It will be recognized that specific circuits (e.g., application specific integrated circuits (ASICs)), one or more processors executing program instructions, or a combination of both, may perform the various actions described herein. Additionally, the sequences of actions described herein can be considered to be embodied entirely within any form of computer readable storage medium having stored therein a corresponding set of computer instructions that upon execution would cause an associated processor to perform the functionality described herein. Thus, the various aspects of the invention may be embodied in a number of different forms, all of which have been contemplated to be within the scope of the claimed subject matter. In addition, for each of the embodiments described herein, the corresponding form of any such embodiments may be described herein as, for example, "logic configured to" perform the described action.

Figure 1:
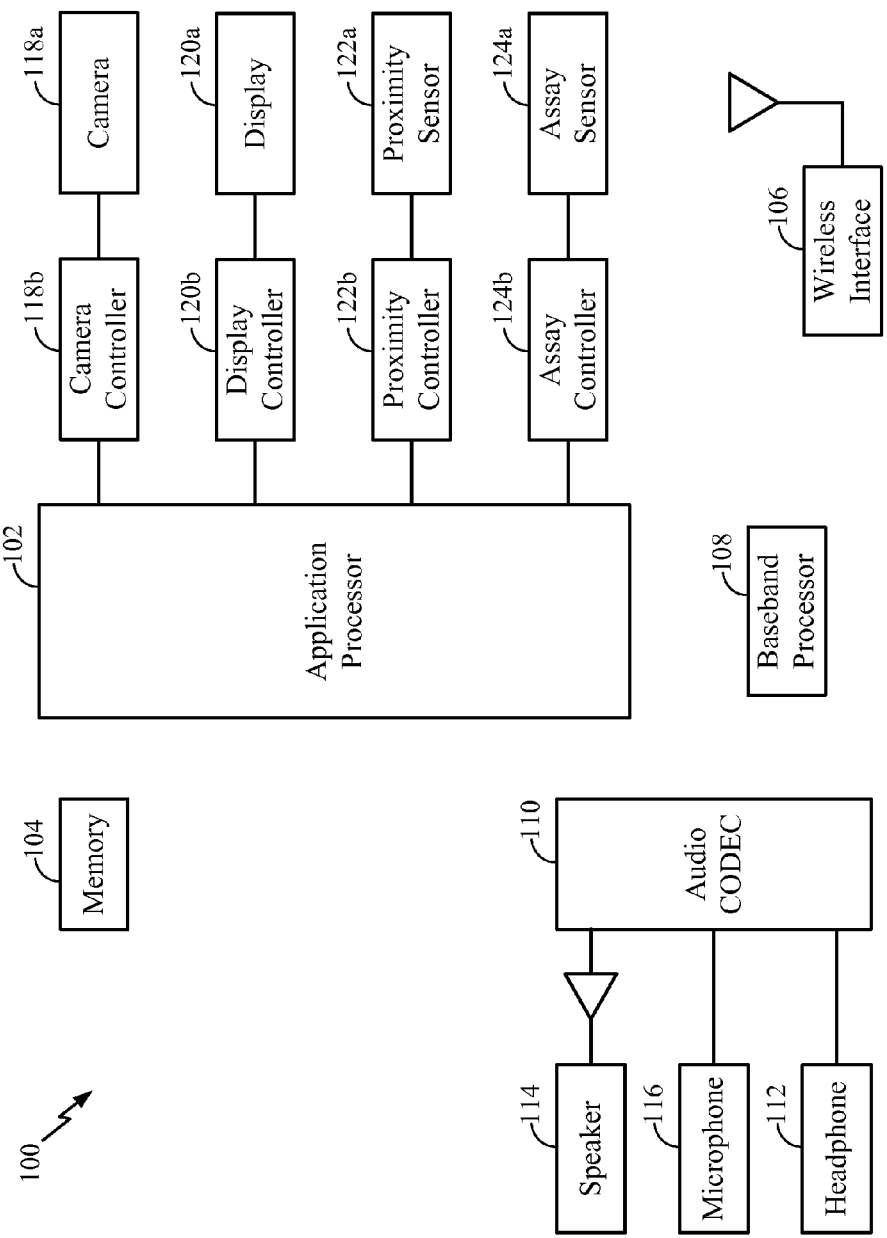
FIG. 1 illustrates a wireless communication device according to an embodiment.

FIG. 1 illustrates a wireless communication device 100 in which embodiments may find application. Shown in FIG. 1 are various modules or components: an application processor 102; a memory 104; a wireless interface 106; a baseband processor 108; an audio codec 110 to provide audio to a headphone 112 or a speaker 114, or to process audio from a microphone 116; a camera 118a and its associated driver, camera controller 118b; a display 120a and its associated driver, display controller 120b; a proximity sensor 122a and its associated driver, proximity controller 122b; and an assay sensor 124a and its associated driver, assay controller 124b.

The assay sensor 124a and the assay controller 124b, and the way in which information obtained from the assay sensor 124a interacts with other modules, are described in the description of the embodiments. However, the other modules shown in FIG. 1 are well known in the art of wireless communication devices, such as cell phones, and therefore such modules need not be described in detail when describing embodiments.

The combination of modules in FIG. 1 serves as an abstraction of a system for wireless communication, such as a smartphone. Interconnects between some of the modules are not show for ease of illustration. Some of the modules may be integrated on a single chip (die), and may be integrated with the application processor 102. The memory 104 abstracts a memory hierarchy, where for example the memory hierarchy may include a cache integrated on the same die as the application processor 102, and NAND flash residing on another die. For ease of illustration, only one module (the memory 104) is used in FIG. 1 to illustrate the memory hierarchy.

The assay sensor 124a is designed to detect or measure one or more analytes. For example, the assay sensor 124a may be designed as an electronic nose to detect or measure various components of a user's breath. The following are particular examples for which the analysis of a user's breath or excessive breath odor may provide indicators of possible health issues. For asthma, nitric oxide levels rise in a user's breath when airways are inflamed. For those with stomach ulcers, the gut bacteria H. Pylori, when mixed with a chemical tracer, emits a carbon isotope. In lung cancer, tumors create dozens of unique volatile organic compounds. Elevated levels of acetone in breath indicate ketosis, which reflects insufficient glucose. This may indicate diabetes. An electronic nose can be designed to recognize ammonia or an ammonia-like odor linked to renal failure, thereby indicating the presence of kidney disease. In liver disease, patients whose livers do not metabolize a tracer solution containing methacetin show changes in carbon dioxide levels. Elevated hydrogen in breath may indicate bacterial overgrowth in the small intestine, which may be an indication of irritable bowel syndrome. For those with lactose malabsorption, bacteria ferments undigested lactose in the colon, thereby raising hydrogen breath levels. For those who have undergone heart transplants, organ rejection creates an oxidative stress that produces alkanes and methylakanes in breath.

Accordingly, the above discussion illustrates that analytes indicating health issues include nitric oxide, carbon isotopes, volatile organic compounds, acetone, ammonia-like odor, carbon dioxide, hydrogen, alkanes, and methylakanes. However, these are just several possible examples of analytes for which the assay sensor 124a may be designed to detect, and other analytes may be detected or measured for an embodiment. For example, alcohol in a user's breath may be detected or measured to determine if the user's blood alcohol concentration is above the legal limit to operate a motor vehicle.

The wireless communication device 100 may be a cell phone, such as for example a smart phone. The user of the communication device 100 may activate the assay sensor 124a by initiating or receiving a phone call, by running an application on the application processor 102, or by touching a touch screen, to name just a few examples.

The assay sensor 124a may also be designed to detect body odor, low electrolyte level due to rigorous physical activity, or the user's temperature. The latter example, measuring or detecting temperature, is not an example of measuring or detecting an analyte. Consequently, the term assay sensor is to be interpreted broadly so that it may encompass a device for measuring or detecting temperature.

Various thresholds may be set for the above-described measurements before a warning or message is generated. The application processor 102 may set the thresholds, and for some embodiments, the application processor 102 may set the thresholds in an adaptive manner.

For example, suppose the assay sensor 124a is designed to detect if the user may have diabetes. For those with diabetes, the breakdown of excess Acetyl CoA from fatty acid metabolism can lead to above normal levels of acetone in the blood. This acetone is excreted through urine and exhaled through the lungs. Acetone concentrations for those without diabetes range from 0.3 to 0.9 parts per million (ppm), but for those with type 2 diabetes, concentrations can rise to more than 1.8 ppm. For type 1 diabetes, the acetone concentration can be even higher.

However, because the user's mouth is some distance away from the microphone 116, and this distance will vary depending upon how the user holds the wireless communication device 100, the threshold for detecting type 1 diabetes may need to be adjusted depending upon the distance from the user's mouth to the assay sensor 124a. For example, if the user's mouth is at a relatively large distance from the assay sensor 124a, then some fresh air may be mix with the user's breath, thereby diluting the acetone concentration. In that case, the threshold would need to be lowered to maintain the same probability of detection for a given false alarm rate. The thresholds may be computed beforehand and stored in a lookup table, indexed by distance. The distance may be measured by the proximity sensor 122a.

For some embodiments, the loudness of the user's voice picked up by the microphone 116 may be measured, and this measurement may be used instead of relying upon the proximity sensor 122a. For example, an application running on the application processor 102 may prompt the user through a calibration procedure, whereby the user is asked to speak at a normal tone of voice at some given distance from the microphone 116. The resulting measurements sets a baseline for estimating the distance between the user's mouth and the microphone 116 based upon the amplitude of the digitized voice waveform.

Figure 2:
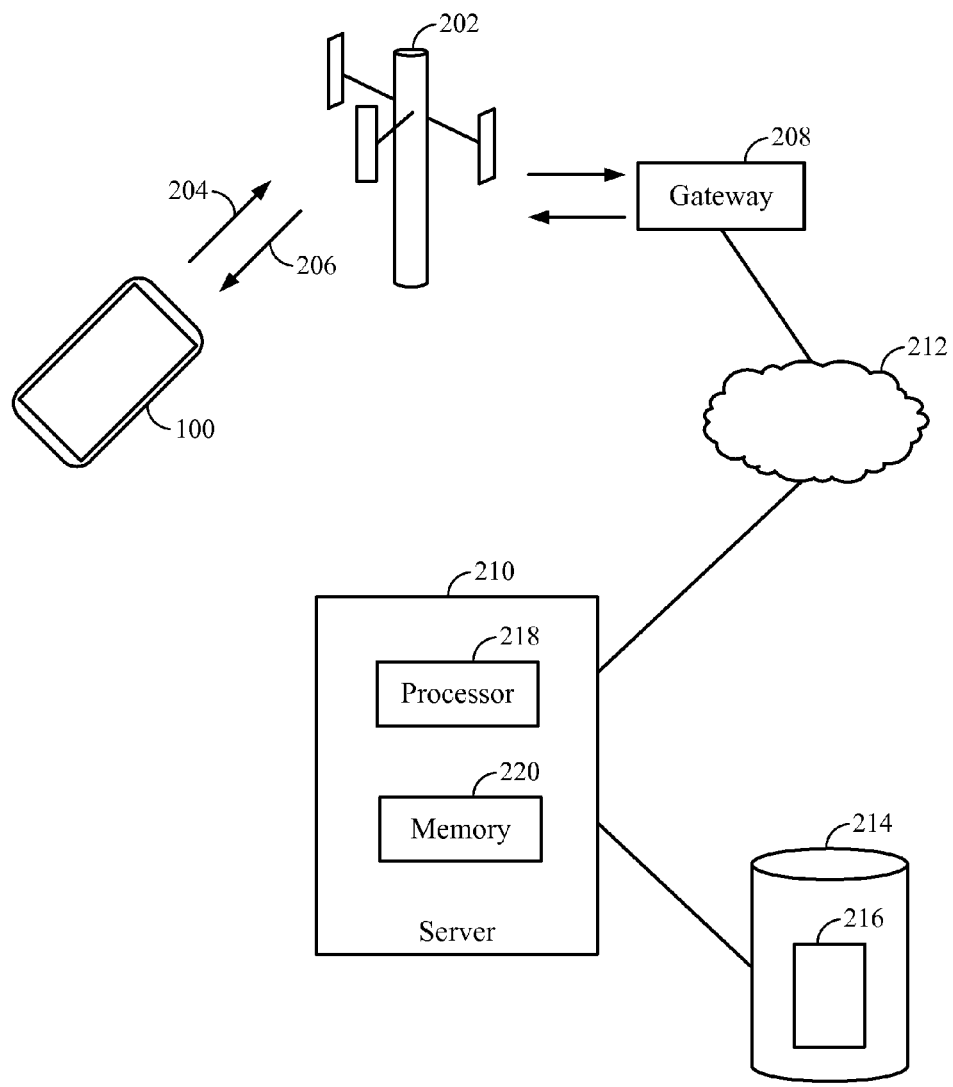
FIG. 2 illustrates a system according to an embodiment.

For some embodiments, the wireless communication device 100 with the assay sensor 124a works in conjunction with a cloud server to provide a system for monitoring various health attributes of a user, and possibly alerting medical personnel regarding the user's health. FIG. 2 illustrates a system comprising the wireless communication device 100, such as a smartphone, and a base station 202. The wireless communication device 100 is located within the cell associated with the base station 202. Arrows 204 and 206 pictorially represent the uplink channel and the downlink channel, respectively, by which the wireless communication device 100 communicates with the base station 202. The system of FIG. 2 further includes a gateway 208, allowing the wireless network comprising the wireless communication device 100 and the base state 202 to communicate with a cloud server 210 (which may include a conventional server) by way of the Internet (cloud) 212. The system of FIG. 2 is of course illustrated in a simplified fashion, but the illustration is sufficient to disclose embodiments.

For some embodiments, the assay sensor 124a may provide messages to the cloud server 210, where the messages comprise raw measurements, processed measurements, or detection events. The results of the assay sensor 124a may be stored in a database, where the module 214 pictorially represents the database. The database 214 may comprise records, where a record is a collection of results from the assay sensor 124a over some period of time. Analyzing a record over time may trigger a warning even if individual or time averaged samples do not exceed a threshold.

Shown in FIG. 2 for the cloud server 210 are a processor 218 and a memory 220. For some embodiments, a process running on the processor 218 according to instructions stored the memory 220 creates and stores the record 216 associated with the user of the wireless communication device 100, and may alert the user or perhaps medical personnel if the record 216 indicates a health issue that should be addressed.

The record 216 comprises results with time stamps so that the measurements or detection events provided by the assay sensor 124a may be monitored over time. By tracking over a period of time, embodiments may employ sophisticated processes to make comparisons over time, and to adjust base lines if needed to take into account temporal changes in the user's environment.

For some embodiments, the processes run by the cloud server 210 may instead run on the application processor 102 of the wireless communication device 100, where the database 214 is instead also run on the application processor 102. Regardless of whether the monitoring processes are run on the application processor 102 or on the cloud server 210, embodiments may be designed so that the processes are transparent to the user, except perhaps when the user is warned about a health issue. For some embodiments, the user may enable or disable the messaging of results from the assay sensor 124a, or the assay sensor 124a itself. For some embodiments, the user may adjust the frequency by which the assay sensor 124a monitors the environment, e.g., the user's breath.

The memory 220, just as the memory 104, may represent a memory hierarchy. It is to be understood that the memory 104 or the memory 220 may be referred to as a non-transitory, computer readable storage medium.

Figure 3:
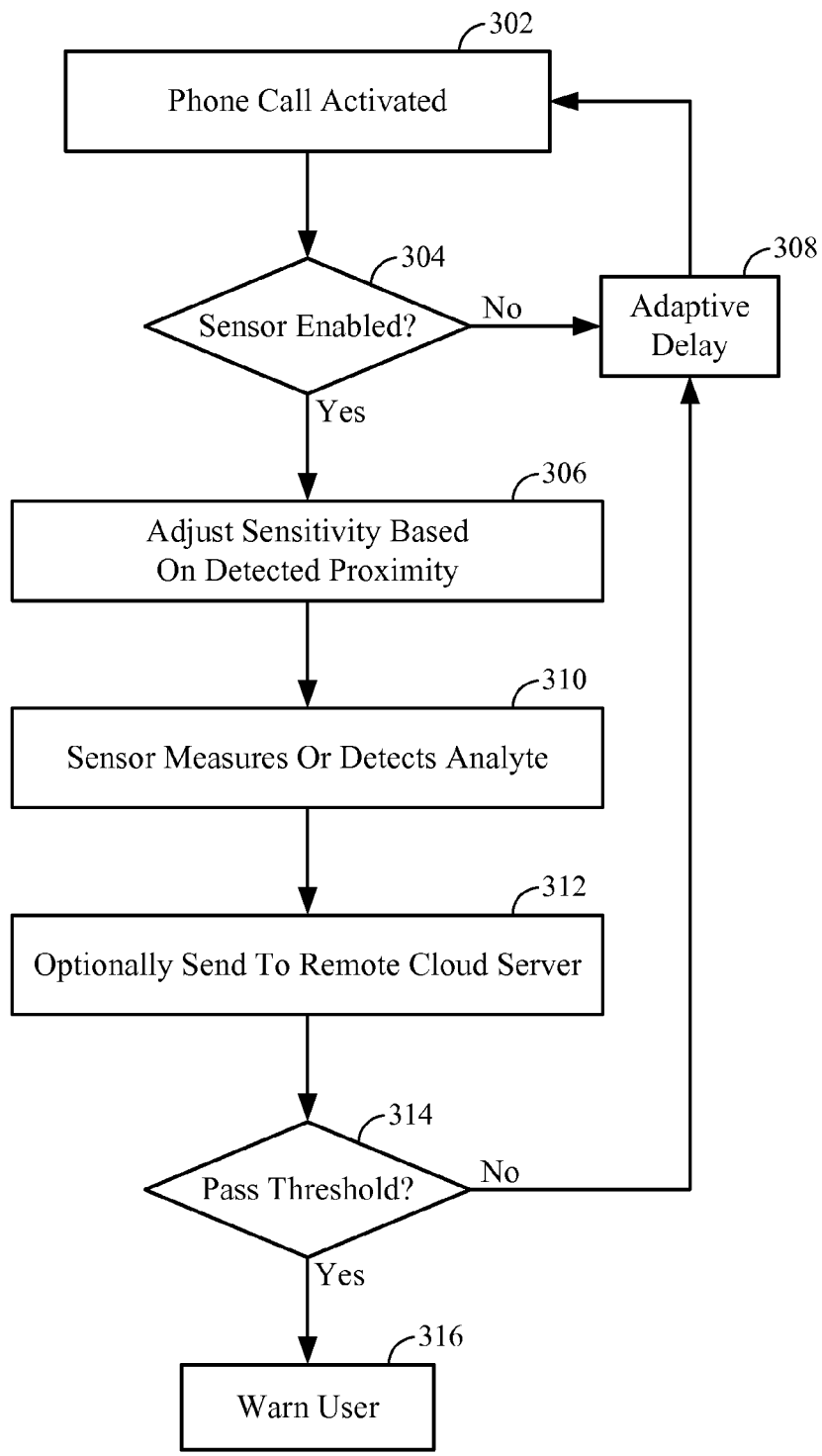
FIG. 3 illustrates a process according to an embodiment.

FIG. 3 illustrates a process according to an embodiment. When a phone call or conversation is activated (302), and if the assay sensor 124a has been enabled (304), then its sensitivity may be adjusted (306). Adjusting the sensitivity may comprise setting a threshold so that the probability of the assay sensor 124a declaring a detection of an analyte is at some desired level. If the assay sensor 124a is not enabled, then after some adaptive delay (308), control is brought back to 302.

Box 310 in FIG. 3 indicates that the assay sensor 124a measures or detects one or more analytes, as discussed previously, in which case if a detection occurs, then a message comprising the results may be sent to a cloud server (312). However, sending a message to a cloud server is optional, and such action may be enabled or disabled by the user.

The decision point 314 represents that a determination is made as to whether the measurement of an analyte exceeds some threshold, or that the record 216 generated by more than one measurement indicates that a threshold has been exceeded. A warning is sent so that the user is warned (316) when such a threshold is exceeded. It is to be understood that a threshold may represent a process applied to the record 216, whereby over time a determination is made as to whether the user should be warned about a health issue.

Those of skill in the art will appreciate that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Further, those of skill in the art will appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The methods, sequences and/or algorithms described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor.

Accordingly, an embodiment of the invention can include a computer readable media embodying a method for measuring and detecting various analytes in a user's breath. Accordingly, the invention is not limited to illustrated examples and any means for performing the functionality described herein are included in embodiments of the invention.

While the foregoing disclosure shows illustrative embodiments of the invention, it should be noted that various changes and modifications could be made herein without departing from the scope of the invention as defined by the appended claims. The functions, steps and/or actions of the method claims in accordance with the embodiments of the invention described herein need not be performed in any particular order. Furthermore, although elements of the invention may be described or claimed in the singular, the plural is contemplated unless limitation to the singular is explicitly stated.

What is claimed is:

1. A wireless communication device comprising:
   a first sensor to detect an analyte associated with a user of the wireless communication device;
   a second sensor to measure a proximity of the wireless communication device to the user's mouth; and
   an application processor to set a detection threshold for the first sensor based upon the measured proximity.

2. The wireless communication device of claim 1, the application processor programmed to warn the user if the detection threshold is exceeded.

3. The wireless communication device of claim 1, the application processor programmed to send a message to a cloud server in response to the first sensor detecting the analyte.

4. The wireless communication device of claim 1, the first sensor comprising an electronic nose.

5. The wireless communication device of claim 1, the analyte selected from the group consisting of nitric oxide, a carbon isotope, ammonia, carbon dioxide, hydrogen, alkanes, and methylakanes.

6. The wireless communication device of claim 1, wherein the first sensor is activated when the user uses the wireless communication device for a phone conversation.

7. The wireless communication device of claim 1, wherein the application processor is configured to adjust the detection threshold according to a distance between the user's mouth and the second sensor measured by the second sensor.

8. The wireless communication device of claim 7, wherein the application processor is configured to decrease the detection threshold as the distance between the user's mouth and tile second sensor increases.

9. The wireless communication device of claim 7, further comprising a lookup table configured to store a plurality of detection thresholds indexed by a plurality of values of distance between the user's mouth and the second sensor, wherein the application processor is configured to reference the lookup table to adjust the detection threshold.

10. A system comprising:
a server; and
a wireless communication device comprising: a first sensor to detect an analyte associated with a user of the wireless communication device;
an application processor programmed to send at least one message to the server, each message in the at least one message in response to the first sensor detecting an analyte in a breath of a user of the wireless communication device; and
a second sensor to measure a proximity of the wireless communication device to the user's mouth, wherein the application processor is programmed to set a sensitivity of the first sensor based upon the measured proximity.

11. The system of claim 10, the server storing the at least one message in a database.

12. The system of claim 11, wherein the at least one message comprises a record of results from the first sensor over a period of time.

13. The system of claim 12, wherein the server provides a warning based on the record of results over the period of time.

14. The system of claim 10, the server generating a warning message in response to the at least one message provided a threshold indicating a health issue is exceeded.

15. The system of claim 10, the analyte selected from the group consisting of nitric oxide, a carbon isotope, ammonia, carbon dioxide, hydrogen, alkanes, and methylakanes.

16. The system of claim 15, the first sensor comprising an electronic nose.

17. The system of claim 10, the analyte selected from the group consisting of nitric oxide, a carbon isotope, ammonia, carbon dioxide, hydrogen, alkanes, and methylakanes.

18. A method comprising: enabling a sensor to detect an analyte in the breath of a user of a wireless communication device, the sensor embedded in the wireless communication device; sending by the wireless communication device at least one message to a cloud server, the at least one message indicating detections of the analyte by the sensor; and generating by the server a warning message if the at least one message exceeds a threshold indicative of a health issue; and setting by an application processor in the wireless communication device the sensitivity of the sensor based upon the proximity of the user's mouth to the wireless communication device.

19. The method of claim 18, wherein the setting by the application processor of the sensitivity of the sensor includes setting a detection threshold, wherein the wireless communication device sends the at least one message in response to the sensor measuring the analyte at a concentration greater than the detection threshold.

20. The method of claim 18, wherein the sensor comprises an electronic nose to detect the analyte in the user's breath.

21. The method of claim 18, the analyte selected from the group consisting of nitric oxide, a carbon isotope, ammonia, carbon dioxide, hydrogen, alkanes, and methylakanes.

22. A wireless communication device comprising:
means for sensing breath, the means for sensing breath to detect an analyte associated with a user of the wireless communication device;
means for sensing proximity, the means for sensing proximity to measure a proximity of the wireless communication device to the user's mouth; and
an application processor to set a detection threshold for the means for sensing breath based upon the measured proximity.

23. The wireless communication device of claim 22, the application processor programmed to warn the user if the detection threshold is exceeded.

24. The wireless communication device of claim 22, the application processor programmed to send a message to a cloud server in response to the means for sensing breath detecting the analyte.

25. The wireless communication device of claim 22, the means for sensing breath comprising an electronic nose.

26. The wireless communication device of claim 22, the analyte selected from the group consisting of nitric oxide, a carbon isotope, ammonia, carbon dioxide, hydrogen, alkanes, and methylakanes.

27. The wireless communication device of claim 22, wherein the means for sensing breath is activated when the user uses the wireless communication device for a phone conversation.

* * * * *